(12) United States Patent
Wan

(10) Patent No.: US 9,149,258 B2
(45) Date of Patent: Oct. 6, 2015

(54) COLLECTION DEVICE WITH DOUBLE OUTPUTS AND METHOD OF USING THE SAME

(76) Inventor: John Wan, San Marino, CA (US)

( * ) Notice: Subject to any disclaimer, the term of this patent is extended or adjusted under 35 U.S.C. 154(b) by 1164 days.

(21) Appl. No.: 13/087,498

(22) Filed: Apr. 15, 2011

(65) Prior Publication Data

US 2012/0264229 A1    Oct. 18, 2012

(51) Int. Cl.
*G01N 1/28* (2006.01)
*G01N 33/48* (2006.01)
*B01L 3/00* (2006.01)
*A61B 10/00* (2006.01)
*G01N 1/40* (2006.01)

(52) U.S. Cl.
CPC .......... *A61B 10/0038* (2013.01); *B01L 3/5029* (2013.01); *B01L 3/50825* (2013.01); *G01N 1/28* (2013.01); *G01N 1/4077* (2013.01); *B01L 2200/0689* (2013.01); *B01L 2300/042* (2013.01); *B01L 2300/044* (2013.01); *B01L 2300/0609* (2013.01); *B01L 2300/0681* (2013.01); *G01N 2001/4088* (2013.01); *Y10T 436/25125* (2015.01)

(58) Field of Classification Search
CPC .............. B01L 3/5029; B01L 3/50825; B01L 2200/0689; B01L 2300/042; B01L 2300/044; B01L 2300/0609; B01L 2300/0681; A61B 10/0038; G01N 1/28; G01N 1/4077; G01N 2001/4088
See application file for complete search history.

(56) References Cited

U.S. PATENT DOCUMENTS

| | | | |
|---|---|---|---|
| 3,083,145 | A | 3/1963 | Ryan |
| 5,514,341 | A | 5/1996 | Urata et al. |
| 6,207,113 | B1 | 3/2001 | Kagaya |
| 2004/0184966 | A1 | 9/2004 | Zhou et al. |
| 2009/0005705 | A1 | 1/2009 | Wan et al. |
| 2009/0036863 | A1* | 2/2009 | Smith et al. ................... 604/408 |

OTHER PUBLICATIONS

U.S. Office Action dated Feb. 7, 2011 issued in US 2009/0005705 A1, to Wan et al., dated Jan. 1, 2009.

* cited by examiner

*Primary Examiner* — Christopher A Hixson
(74) *Attorney, Agent, or Firm* — Scully, Scott, Murphy & Presser. P.C.

(57) ABSTRACT

A collection device with double outputs and a method of using the same are provided. The collection device comprises an accommodating chamber comprising an upper chamber opening, a lower chamber opening and a chamber body therebetween; an inlet member comprising an upper inlet opening, a lower inlet opening and an inlet passage therebetween, said lower inlet opening being connected and communicated with said upper chamber opening; an outlet member comprising an outlet body, a protrusion depending from a lower surface of said outlet body, a first output positioned at a lower end of said protrusion and a second output provided at said lower surface of said outlet body, said lower chamber opening of said accommodating chamber being connected and communicated with said outlet member; a collecting section comprising a handle detachably engageable with said inlet member and a collecting stick attached to the handle, a lower portion of said collecting stick entering into said accommodating chamber through said inlet passage upon engagement of said handle with said inlet member, and a sealing assembly for sealing said first output and said second output.

20 Claims, 10 Drawing Sheets

COLLECTION DEVICE WITH DOUBLE OUTPUTS AND METHOD OF USING THE SAME

BACKGROUND OF THE INVENTION

1. Field of the Invention

The present invention is generally directed to a medical device, particularly to a collection device for fecal specimen.

2. Related Art

The analysis of feces has become a necessary item for diagnosing diseases adopted by the medical units. Except for routine examination, some other necessary chemical tests, for example fecal occult blood ("FOB") will be proceeded according to the patients' condition.

Fecal occult blood is a phenomenon which indicates gastrointestinal hemorrhage. Since a symptom of FOB usually happens when the patients suffers from peptic ulcer and colon polyp which probably transforms into gastrointestinal cancer, the detection of FOB as a physical examination has become accepted by more and more people.

The US pending patent US2009/0005705 published on Jan. 1, 2009 discloses a fecal specimen collector which consists of a top cover, a bottle body, a specimen output and a bottom cover. However, the fecal specimen is detected via only one output of the fecal specimen collector, thus, the conventional collector is generally just applicable with an operator instead of an automatic detection machine to read the detection result.

SUMMARY OF THE INVENTION

The present invention aims to provide a fecal specimen collection device which isn't only applicable to an operator but also to an automatic analyzing device to read the detection result.

The collection device with double outputs comprises an accommodating chamber comprising an upper chamber opening, a lower chamber opening and a chamber body therebetween, an inlet member comprising an upper inlet opening, a lower inlet opening and an inlet passage therebetween, said lower inlet opening being connected and communicated with said upper chamber opening, an outlet member comprising an outlet body, a protrusion depending from a lower surface of said outlet body, a first output positioned at a lower end of said protrusion and a second output provided at said lower surface of said outlet body, said lower chamber opening of said accommodating chamber being connected and communicated with said outlet member, a collecting section comprising a handle detachably engageable with said inlet member and a collecting stick attached to the handle, a lower portion of said collecting stick entering into said accommodating chamber through said inlet passage upon engagement of said handle with said inlet member, and a sealing assembly for sealing said first output and said second output.

In one aspect of the collection device, said accommodating chamber is molded with said inlet member or said outlet member into one piece.

In one aspect of the collection device, a thread portion is provided on a surface of said handle, and a corresponding thread portion is provided on a surface of said inlet passage for the engagement of said handle with said inlet member.

In one aspect of the collection device, said collection device further comprises a filter member provided in said inlet passage, and a filter hole is provided proximately at the center of said filter member.

In one aspect of the collection device, said filer member and said inlet passage are molded into one piece.

In one aspect of the collection device, said filter member further comprises a rim provided at an upper end of said filter member, for being fastened on the edge of said upper inlet opening.

In one aspect of the collection device, said collecting stick further comprises a thread or a brush at a distal end of said collecting stick, and the external diameter of said thread or said brush is substantially equal to the diameter of said filter hole.

In one aspect of the collection device, said handle and said collecting stick of said collecting section are formed integrally.

In one aspect of the collection device, said collecting section further comprises an accommodating slot for accommodating the top of said collecting stick.

In one aspect of the collection device, said sealing assembly comprises at least one of an aluminum foil, a plug and a cap.

In one aspect of the collection device, said sealing assembly comprises a first sealing member in the form of a sealing cap for sealing said first output and a second sealing member for sealing said second output, said first sealing member engaging with said protrusion by threads or snap fit, said first sealing member comprising a projection configured to be inserted into said first output for sealing said first output.

In one aspect of the collection device, said protrusion is formed substantially in the shape of taper, and said first output is concaved from a lower end of said taper into said accommodating chamber.

In one aspect of the collection device, the diameter of said first output is about 0.8-1.5 mm.

In one aspect of the collection device, said handle further comprises a sealing ring therein, said sealing ring being pressed between said inlet member and said handle when said handle engages with said inlet member.

In one aspect of the collection device, said inlet member further comprises a sealing ring along an outer circumference of said lower inlet opening of said inlet member, said sealing ring being pressed between said inlet member and said handle when said handle engages with said inlet member.

In one aspect of the collection device, a sealing ring is provided between said lower chamber opening of said accommodating chamber and said outlet member for sealing.

In one aspect of the collection device, said lower chamber opening of said accommodating chamber engages with said outlet member by jointing, snap fit or interference fit.

In one aspect of the collection device, said accommodating chamber is transparent.

In one aspect of the collection device, the sectional view of said accommodating chamber is substantially oval or round, and the sectional view of said outlet member is the same as that of said accommodating chamber.

In one aspect of the collection device, the collection device can be used by at least one of the followings:

a) manipulating said sealing assembly of said collection device to expose said first output of said collection device, squeezing said chamber body of said accommodating chamber of said collection device to release a specimen dissolved in a buffer fluid of said accommodating chamber from said first output, and analyzing the specimen in the buffer fluid to determine an attribute of the specimen, b) placing said collection device in a detection machine, manipulating said sealing assembly on said second output to release a specimen dissolved in said buffer fluid contained in said accommodating chamber of said collection device, and analyzing the specimen in the buffer fluid to determine an attribute of the specimen.

The present invention also provides a method of handling a collection device, comprising at least one of the followings:

a) manipulating a sealing assembly of a collection device to expose a first output of said collection device comprising:

i) an accommodating chamber comprising an upper chamber opening, a lower chamber opening and a chamber body therebetween, ii) an inlet member comprising an upper inlet opening, a lower inlet opening and an inlet passage therebetween, said lower inlet opening being connected and communicated with said upper chamber opening, iii) an outlet member comprising an outlet body, a protrusion depending from a lower surface of said outlet body, a first output positioned at a lower end of said protrusion and a second output provided at said lower surface of said outlet body, said lower chamber opening of said accommodating chamber being connected and communicated with said outlet member, iv) a collecting section comprising a handle detachably engageable with said inlet member and a collecting stick attached to the handle, a lower portion of said collecting stick entering into said accommodating chamber through said inlet passage upon engagement of said handle with said inlet member, and v) a sealing assembly for sealing said first output and said second output, squeezing said chamber body of said accommodating chamber of said collection device to release a specimen dissolved in a buffer fluid of said accommodating chamber from said first output, and analyzing the specimen in the buffer fluid to determine an attribute of the specimen;

b) placing said collection device in a detection machine;

manipulating a sealing assembly on said second output to release a specimen dissolved in said buffer fluid contained in said accommodating chamber of said collection device, and analyzing the specimen in the buffer fluid to determine an attribute of the specimen.

The advantage of the present invention is that the collection device of the present invention has two outputs formed on the outlet member, therefore, the detection of gastrointestinal hemorrhage can be achieved by the collection device of the present invention cooperating with analyzing device. Moreover, the double outputs of the collection device of the present invention are respectively applicable to manually detect the specimen by operator or automatically detect by a machine.

The collection device in one aspect of the present invention also has a filter member which provides a filter hole therein for removing the excessive feces. The collection device also can quantify the collected fecal specimen. Moreover, the collection device is designed to prevent sealing by providing a sealing member configured at the joint of the adjacent members. Further, the property of the collected feces can be observed through accommodating chamber of the present invention.

The diameter of the first output on the protrusion is about 0.8-1.5 mm, and the output is concaved from the top of protrusion into the accommodating chamber for preventing specimen leaking from the first output without any outside force. Moreover, the liquid volume released from the first output is also under control due to the structure of the first output.

DETAILED DESCRIPTION OF EXEMPLARY EMBODIMENT OF THE INVENTION

The present invention provides a collection device with double outputs, which is used for collecting biological fecal specimen. The structure of the collection device and its use will be described in detail hereinafter with reference to the examples of collection device for collecting fecal specimen.

Example 1

Figure 1:
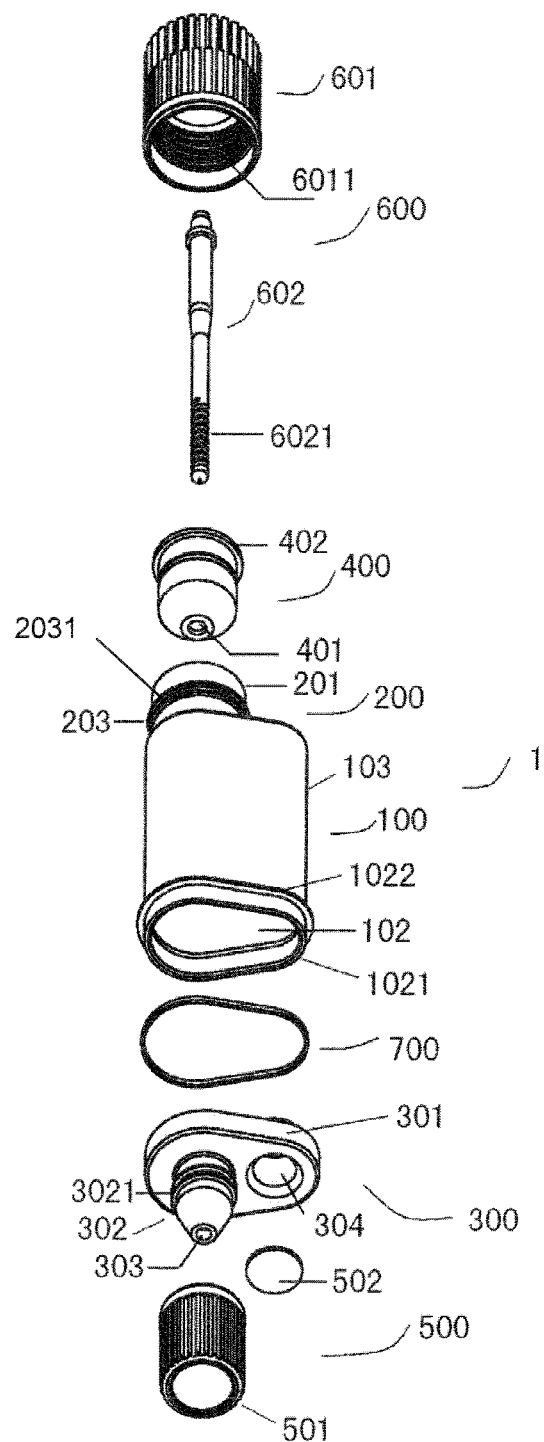
FIG. 1 is an exploded perspective view of the collection device according to the example 1 of the present invention.
Figure 2:
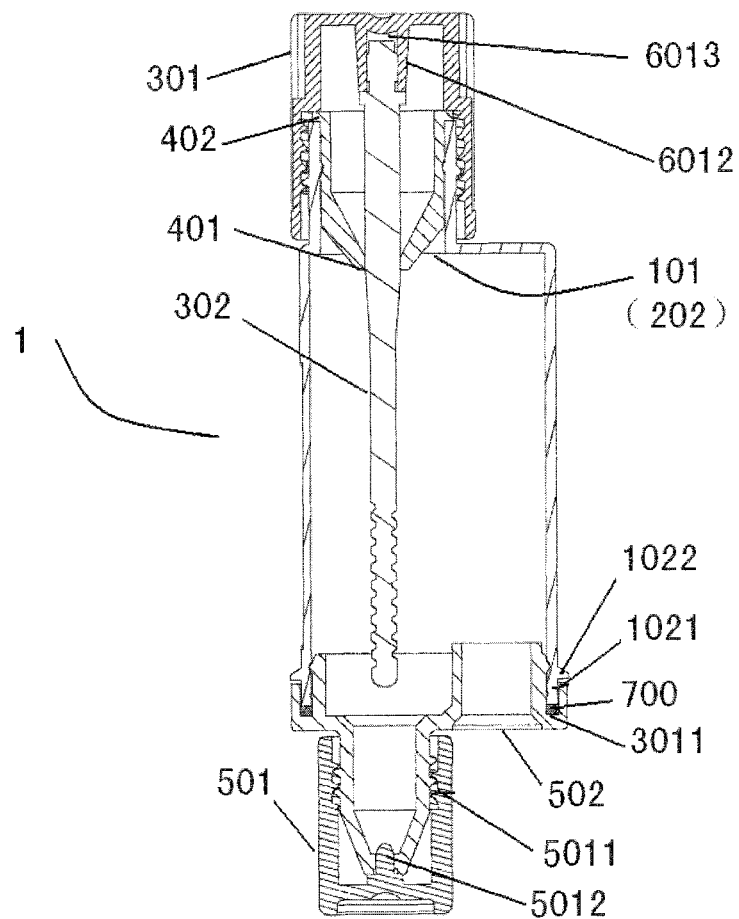
FIG. 2 is a sectional view of the collection device according to the example 1 of the present invention.

Referring to the collection device 1 with double outputs shown in FIG. 1 and FIG. 2, the collection device 1 comprises an accommodating chamber 100, an inlet member 200, an outlet member 300, a sealing assembly 500 and a collecting section 600.

The accommodating chamber 100, in the shape of hollow tubular, comprises an upper chamber opening 101, a lower chamber opening 102 and a chamber body 103 therebetween. An extending wall 1021 extends downwards from the lower chamber opening 102 and a flange 1022 extends outwards from the periphery of the lower chamber opening 102.

The inlet member 200, in the shape of hollow tubular, comprises an upper inlet opening 201, a lower inlet opening 202 and an inlet passage 203 therebetween, and an external thread 2031 is provided at the outer surface of the inlet passage 203. In the present example, the inlet member 200 and the accommodating chamber 100 are molded as one piece, i.e. the lower inlet opening 202 of the inlet member 200 is connected and communicated with the upper chamber opening 101 of the accommodating chamber 100.

The output member 300 comprises an outlet body 301, a protrusion 302 protruding from the lower surface of the outlet body 301, a first output 303 provided at the top of the protrusion 302 and a second output 304 provided at the lower surface of the outlet body 301, and both the first output 303 and the second output 304 are communicated with the inner of the accommodating chamber 100. In this example, the protrusion 302, substantially in the shape of taper, comprises an external thread 3021 provided on the outer surface of the protrusion 302. The first output 303 at the top of the taper is concaved from the top of the taper to the accommodating chamber 100. The diameter of the first output is about 0.8-1.5 mm. The outlet body 301 comprises a slot 3011 formed in the sidewall of the outlet body 301, for receiving the extending wall 1021 at the lower chamber opening 102 of the accommodating chamber 100. When the extending wall 1021 is inserted into the slot 3011, the flange 1022 covers on the edge of the slot 3011 to fasten the outlet member 300, such that the accommodating chamber 100 and the output member 300 are combined with each other. In the present example, a sealing ring 700 is provided at the bottom of the slot 3011 and takes effect to seal when the accommodating chamber 100 and the output member 300 are combined with each other. Alternatively, the slot 3011 also may not be provided in the outlet body 301, but the extending wall 1021 of the accommodating chamber 100 is directly inserted into inner space of the outlet body 301 for engaging therewith.

It can been seem from the sectional view of the collection device 1 shown in the FIG. 2, the sealing assembly 500 at the bottom of the collection device 1 comprises a first sealing member 501 and a second sealing member 502 which respectively cover on the first output 303 and the second output 304 of the outlet member 300. In particular, an internal thread 5011 is provided on the inner surface of the first sealing member 501, and a projection 5012 is provided at the proximal center of the inner lower surface of the first sealing member 501. The projection 5012 is inserted into the first output 303 when the internal thread 5011 engages with the external thread 3021 of the protrusion 302, so that the first output 303 is blocked. Alternatively, the above thread also can be replaced by snap fit components which are respectively provided in inner surface of the first sealing member 501 and the protrusion 302, so that the first output 303 and the first sealing member 501 are engaged together. In this example, the first sealing member 501 is a sealing cap covering the first output 303, and the second sealing member 502 is an aluminum foil covering the second output 304, so that the first output 303 and second output 304 are sealed respectively.

A collecting section 600 comprises a handle 601 and a collecting stick 602. An internal threaded portion 6011 is provided on the inner surface of the handle 601, and engages with the external threaded portion 2031 of the inlet member 200, such that the collection section 600 and the inlet member 200 are combined with each other. An accommodating slot 6013 is formed in a hollow cylinder 6012 extending from the proximal center of the upper surface of the inner of the handle 601. The top of the collecting stick 602 is received in the accommodating slot 6013, so that the handle 601 and the collecting stick 602 are engaged with each other. A threaded portion 6021, alternatively a brush, is provided at the distal end of the collecting stick 602 for collecting feces. The lower portion of the collecting stick 602 enters into the chamber body 103 through the inlet passage 203 of the inlet member 200.

In the present example, the collection device 1 further comprises a filter member 400 disposed within the inlet passage 203 through the upper inlet opening 201 of the inlet member 200. The filter member 400, in the shape of hollow tubular, is made from rubber and comprises a central filter hole 401 and a rim 402. The filter hole 401 is provided at the center of the lower end of the filter member 400, and the diameter of the filter hole 401 is substantially equal to the outer diameter of the threaded portion 6021 of the collecting stick, such that the excessive feces could be removed when the collecting stick 602 of the collecting section 600 goes through the filter hole 401 of the filter member 400. The rim 402 of the filter member 400 is provided on the edge of the outer circumference of the filter member 400. When the filter member 400 is received in the inlet passage 203, the rim 402 firmly covers on the edge of the filter member 400, so that the rim 402 functions as a sealing ring.

The use of the collection device will be illustrated in the following:

During operating, the operator first takes out the collecting section 600 engaging with the upper inlet opening 201 by rotating the handle 601, then holds the handle 601, and collects feces through the collecting stick 602. After the collecting stick 602 goes though the filter hole 401 of the filter member 400, the operator rotates the feces collector 600 onto the accommodating chamber 100 though the engagement of the internal threaded portion 6011 of the handle 601 with the external thread 2031 of the inlet member 200, so that the collecting section 600 tightly engages with the accommodating chamber 100. As the excessive feces is removed through the filter hole 401 of the feces collector 600, the feces to be detected enters the chamber body 103 and is dissolved in the buffer of the chamber body 103.

During manual examination, the examiner first unscrews the first sealing member 501, then squeezes the chamber body 103 of the accommodating chamber 100. After that, the liquid of the accommodating chamber 100 drops onto an analyzing device (not shown). The liquid reacts at the analyzing device, and then, the results appear on the analyzing device so as to indicate whether the fecal specimen is positive or negative.

During examination by an automatic detection machine (not shown), the collection device is first positioned on the automatic detection machine, then the aluminum foil 502 covering the second output 304 is pierced by a piercing device of the automatic detection machine. After the liquid dissolving fecal specimen drops onto an analyzing device and reacts at the analyzing device, the results appears on the analyzing device so as to indicate whether the fecal specimen is positive or negative.

Example 2

Figure 3:
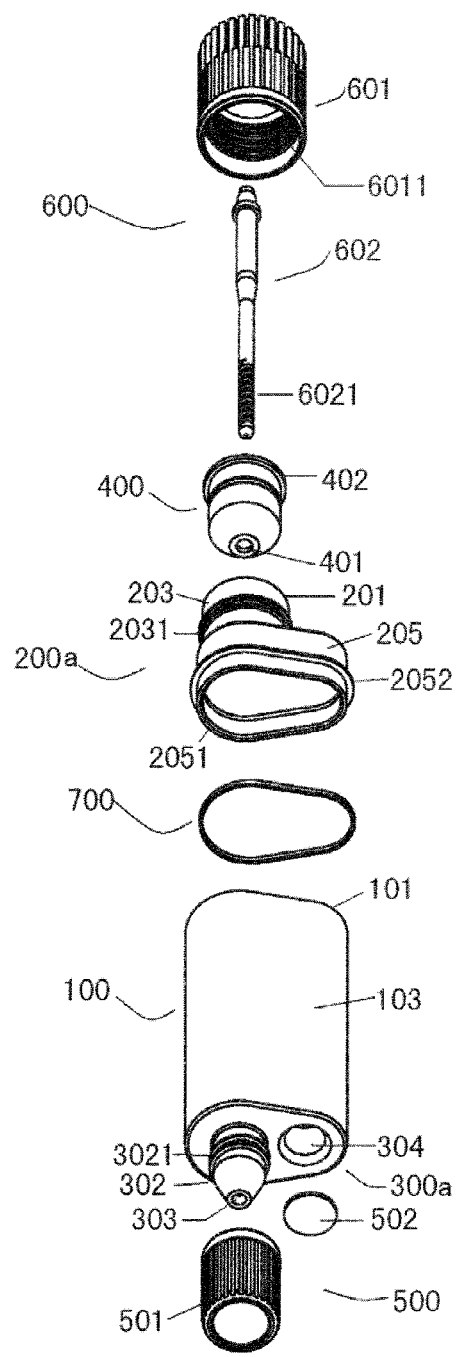
FIG. 3 is an exploded perspective view of the collection device according to the example 2 of the present invention.
Figure 4:
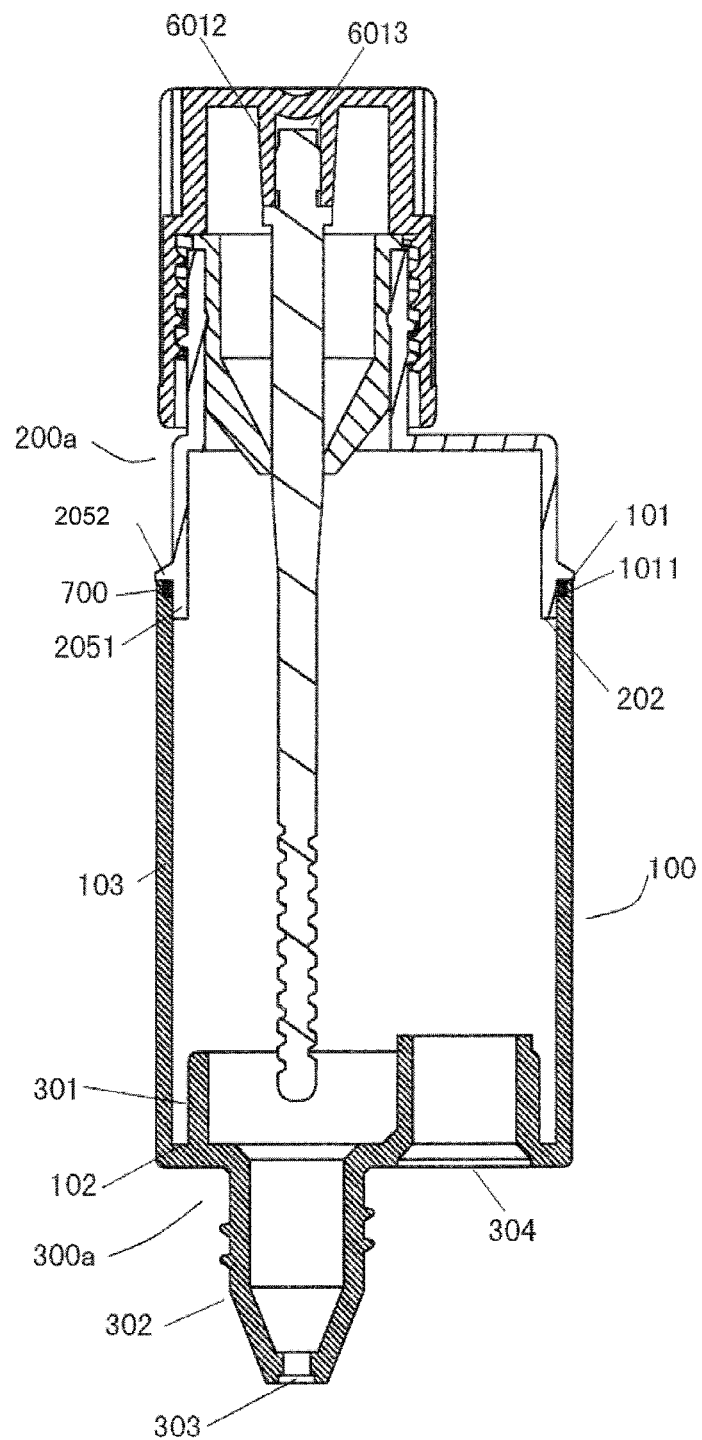
FIG. 4 is an exploded perspective view of a part of the collection device according to the example 2 of the present invention.

FIG. 3 and FIG. 4 illustrates an exploded perspective view of the collection device in example 2. The present example is similar to the first example, with the difference that the accommodating chamber 100 and the outlet member 300a are formed integrally at the lower portion of the chamber body 103. The inlet member 200a comprises an inlet passage 203 and an inlet body 205. An external thread 2031 is provided on the outer surface of the inlet passage 203. An extending wall 2051 extends downwards from the lower opening of the inlet body 205, and a flange 2052 extends outwards from the periphery of the lower opening of the inlet body 205. The outer circumference of the extending wall 2051 is dimensionally almost equal to the inner circumference of the chamber body 103. When the extending wall 2051 is inserted into the chamber body 103, the flange 2052 firmly covers on the edge of the upper chamber opening 101 of the accommodating chamber 100, so that the accommodating chamber 100 and the inlet member 200 are engaged together. Further, a groove 1011, in which the sealing ring 700 is held, is formed at the inner edge of the upper opening 101 of the accommodating chamber 100. The accommodating chamber is sealed by the sealing ring 700 when the accommodating chamber 100 engages with the inlet member 200. When the filter member 400 is received in the inlet passage 203, the rim 402 firmly covers on the upper inlet opening 201, so that the rim 402 functions as a sealing ring.

In the example 1 and example 2, the sectional view of the accommodating chamber 100 is in the shape of oval, and the sectional view of the outlet member 300a is the same as that of the accommodating chamber 100. The other parts of the collection device and the use of the collection device will not be stated hereinafter for they are as same as that of the example 1.

Example 3

Figure 5:
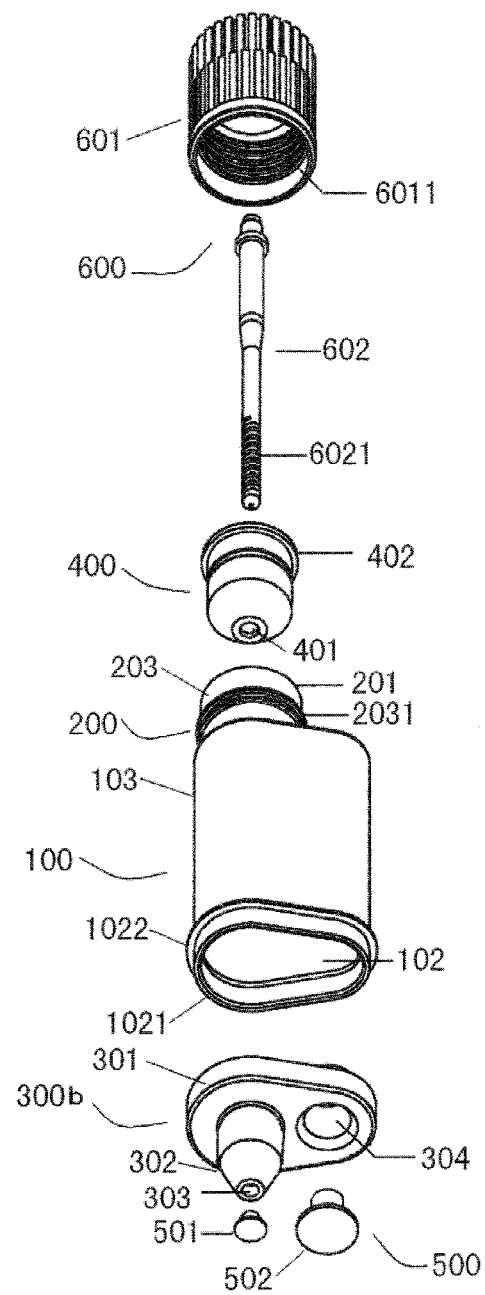
FIG. 5 is an exploded perspective view of the collection device according to the example 3 of the present invention.

Referring to FIG. 5, the present example is similar to the example 1. The difference is that the accommodating chamber 100 and the outlet member 300b are combined by jointing, snap fit or interference fit, without sealing ring therebetween. Moreover, no thread is provided on the protrusion 302 of the outlet member 300b. Both the first sealing member 501 and the second sealing member 502 are plugs which are respectively inserted into the first output 303 and the second output 304.

Example 4

Figure 6:
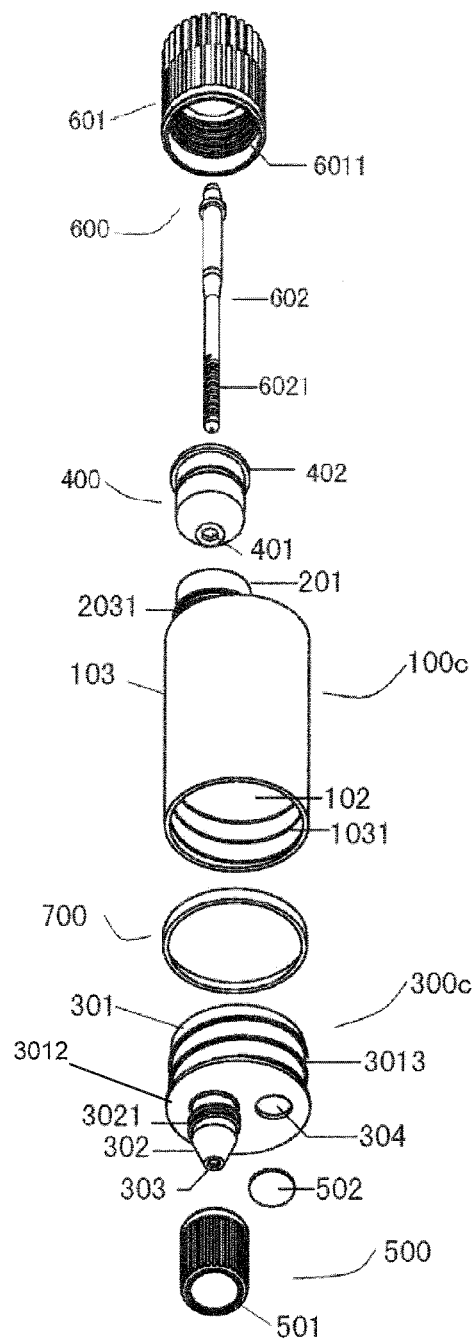
FIG. 6 is an exploded perspective view of the collection device according to the example 4 of the present invention.

Referring to FIG. 6, the present example is similar to the example 1. The difference is that the sectional view of the accommodating chamber 100c is round in shape. The sectional view of the outlet member 300c is the same as that of the accommodating chamber. An external thread 3013 is provided on the outer surface of the outlet body 301 of the outlet member 300c, and a corresponding internal thread 1031 for engaging the external thread 3013 is provided adjacent to the lower opening 102 of the chamber body 103 of the accommodating chamber 100c. A flange 3012 for holding a sealing ring 700 thereon extends outwards from the outer circumference of the lower surface of the outlet body 301 of the outlet member 300c. The sealing ring 700 takes effect on sealing when the accommodating chamber 100c and the outlet member 300c are engaged with each other.

Example 5

Figure 7:
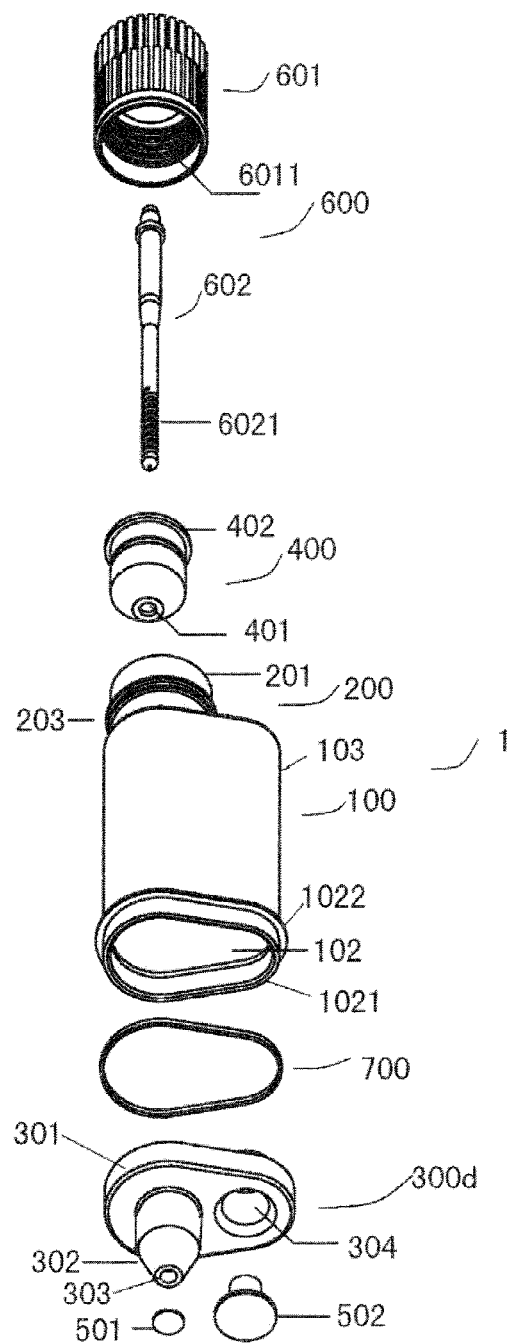
FIG. 7 is an exploded perspective view of the collection device according to the example 5 of the present invention.

Referring to FIG. 7, the present example is similar to the example 1. The difference is that no thread is provided on the protrusion 302 of the outlet member 300d, the first sealing member 501 is an aluminum foil which covers on the first output 303, and the second sealing member 502 is a plug which inserts into the second output 304. The specimen dissolved in the buffer of the accommodating chamber is released after the aluminum foil is pierced.

Example 6

Figure 8:
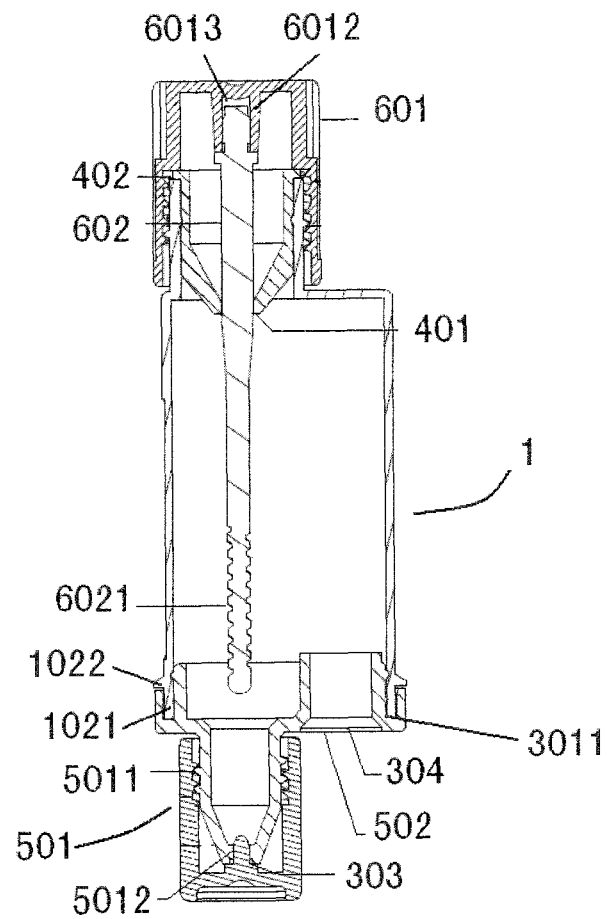
FIG. 8 is an exploded perspective view of the collection device according to the example 6 of the present invention.

Referring to FIG. 8, the present example is similar to the example 1. The difference is that in the present example, the extending wall 1021 of the lower opening 102 directly contacts the bottom of the slot 3011 of the outlet member 300, without the sealing ring 700 in the slot 3011.

Example 7

Figure 9:
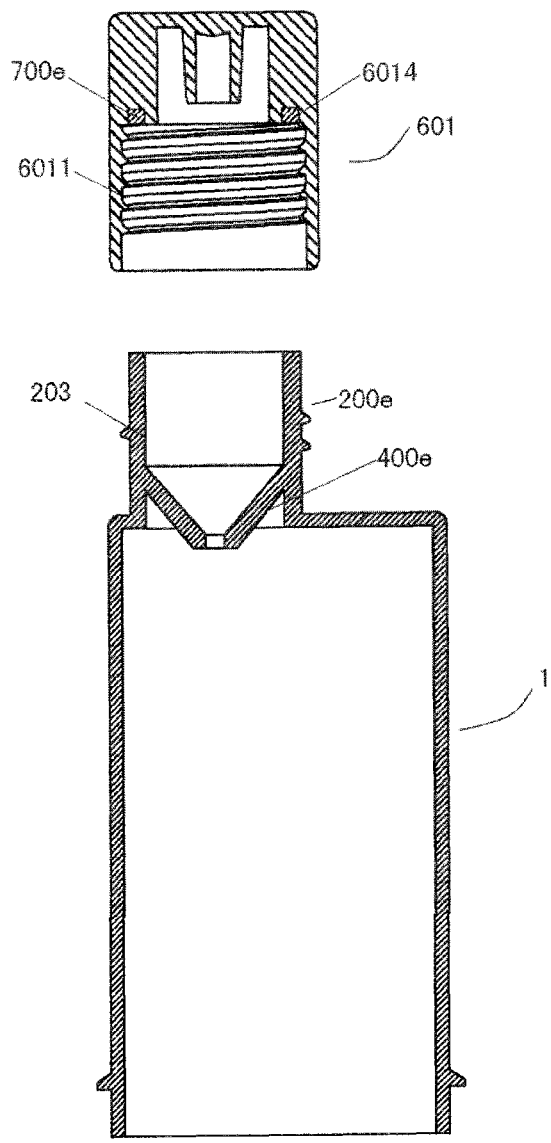
FIG. 9 is an exploded sectional view of a part of the collection device according to the example 7 of the present invention.

Referring to FIG. 9, the present example is similar to the example 1. The difference is that the filter member 400e has no rim, and is molded integrally with the inlet passage 203 of the inlet member 200e, i.e. the filter member 400e and the inlet passage 203 of the inlet member 200e have a common outer wall. A groove 6014 for holding a sealing ring 700e is provided between the internal thread 6011 of the inner surface of the handle 601 and the top of the handle 601. The sealing ring 700e takes effect on sealing when the handle 601 engages with the inlet member 200e, so that the leakage of liquid is prevented.

Example 8

Figure 10:
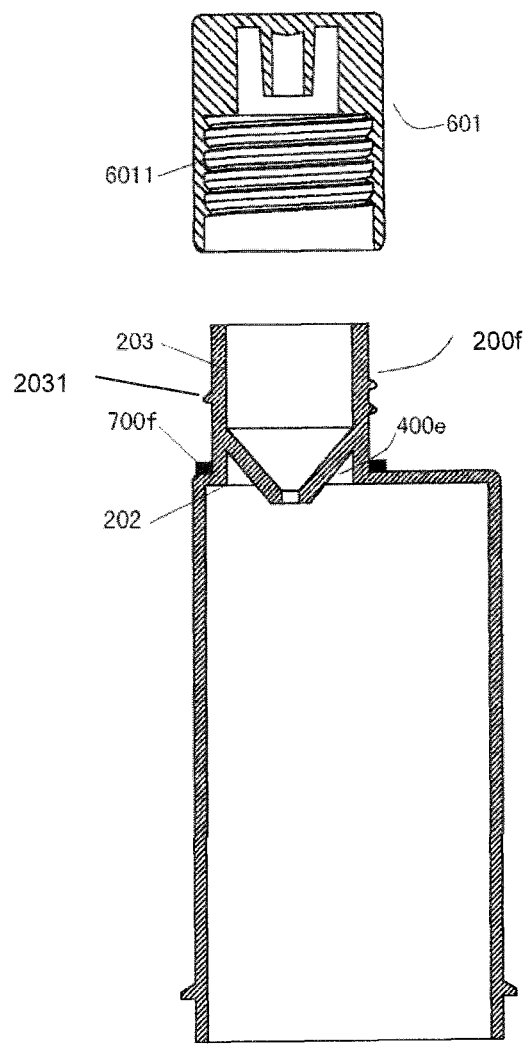
FIG. 10 is an exploded sectional view of a part of the collection device according to the example 8 of the present invention.

Referring to FIG. 10, the present example is similar to the example 7. The difference is that a sealing ring 700f is further provided around the outer circumference of the lower inlet opening 202 of the inlet member 200f. The sealing ring 700f takes effect on sealing for preventing liquid leakage when the sealing ring 700f is pressed due to the internal thread 6011 of the handle 601 engaging with the external thread 2031 of the inlet member 200f.

The collection device of the present invention can be variedly transformed by a person in the art, for example, the handle and the collecting stick of the collecting section can be molded into one piece; the filter member and the accommodating chamber can be formed into one piece; alternatively, the filter member and the inlet passage can be formed into one piece. The engagement of the present invention can be achieved by the thread, optionally, snap fit and interference fit. Further, the shape of the accommodating chamber isn't limited to the shape illustrated in the accompanying drawings. The accommodating chamber can be transparent for easily observing the specimen in the chamber. Every part of the collection device can be made from ABS resin, polypropylene or polythene plastic.

There are two outputs formed on the outlet member or accommodating chamber of the present invention, thereby, the detection of gastrointestinal hemorrhage is achieved by the collection device of the present invention cooperating with detection device. The two outputs in the present invention can respectively be applicable to the manual examination and machine examination. The above collection devices are examples for collecting feces, whereas the collection device of the present invention also can be used to collect other biological excrement.

The above embodiments are provided just as preferable examples of the present invention, not as limitation to the present invention. It should be noted that all equivalent structural variations according to the description and drawings of the present invention fall within the protection scope of the present invention.

What is claimed is:

1. A collection device with double outputs, comprising:
   an accommodating chamber comprising an upper chamber opening, a lower chamber opening and a chamber body therebetween,
   an inlet member comprising an upper inlet opening, a lower inlet opening and an inlet passage therebetween, said inlet member having an upper edge at said upper inlet opening, said lower inlet opening being connected and communicated with said upper chamber opening,
   an outlet member comprising an outlet body, a protrusion depending from a lower surface of said outlet body, a first output positioned at a lower end of said protrusion and a second output provided at said lower surface of said outlet body, said lower chamber opening of said accommodating chamber being connected and communicated with said outlet member,
   a collecting section comprising a handle detachably engageable with said inlet member and a collecting stick attached to the handle, a lower portion of said collecting stick entering into said accommodating chamber through said inlet passage upon engagement of said handle with said inlet member, two sealing assemblies for sealing said first output and said second output, respectively, and a filter member provided in said inlet passage, wherein said filter member comprises a tubular wall extending between the upper inlet opening and the lower inlet opening of said inlet member, said tubular wall defining a filter hole proximately at the center of said filter member, said filter hole being dimensioned to allow said lower portion of said collecting stick to pass through said filter hole, and wherein said filter member further comprises a rim extending radially from said tubular wall onto said upper edge of said inlet member, wherein said rim provides a sealing between said handle and said inlet member when said handle engages said inlet member.

2. The collection device of claim 1, wherein said accommodating chamber is molded with said inlet member or said outlet member into one piece.

3. The collection device of claim 1, wherein a thread portion is provided on a surface of said handle, and a corresponding thread portion is provided on a surface of said inlet passage for the engagement of said handle with said inlet member.

4. The collection device of claim 1, wherein said filer filter member and said inlet passage are molded into one piece.

5. The collection device of claim 1, wherein said collecting stick further comprises a thread or a brush at a distal end of said collecting stick, and the external diameter of said thread or said brush is substantially equal to the diameter of said filter hole.

6. The collection device of claim 1, wherein said handle and said collecting stick of said collecting section are formed integrally.

7. The collection device of claim 1, wherein said collecting section further comprises an accommodating slot for accommodating the top of said collecting stick.

8. The collection device of claim 1, wherein said sealing assembly comprises at least one of an aluminum foil, a plug and a cap.

9. The collection device of claim 1, wherein said sealing assembly comprises a first sealing member in the form of a sealing cap for sealing said first output and a second sealing member for sealing said second output, said first sealing member engaging with said protrusion by threads or snap fit, said first sealing member comprising a projection configured to be inserted into said first output for sealing said first output.

10. The collection device of claim 1, wherein said protrusion is formed substantially in the shape of taper, and said first output is concaved from a lower end of said taper into said accommodating chamber.

11. The collection device of claim 1, wherein said handle further comprises a sealing ring therein, said sealing ring being pressed between said inlet member and said handle when said handle engages with said inlet member.

12. The collection device of claim 1, wherein said inlet member further comprises a sealing ring along an outer circumference of said lower inlet opening of said inlet member, said sealing ring being pressed between said inlet member and said handle when said handle engages with said inlet member.

13. The collection device of claim 1, wherein a sealing ring is provided between said lower chamber opening of said accommodating chamber and said outlet member for sealing.

14. The collection device of claim 1, wherein said lower chamber opening of said accommodating chamber engages with said outlet member by jointing, snap fit or interference fit.

15. The collection device of claim 1, wherein said accommodating chamber is transparent.

16. The collection device of claim 1, wherein the sectional view of said accommodating chamber is substantially oval or round, and the sectional view of said outlet member is the same as that of said accommodating chamber.

17. A method of operating a collection device with double outputs comprising:

providing the collection device described by claim 1; and operating the device by either a) manipulating said sealing assembly on said first output of said collection device to expose said first output of said collection device, squeezing said chamber body of said accommodating chamber of said collection device to release a specimen dissolved in a buffer fluid of said accommodating chamber from said first output, and analyzing the specimen in the buffer fluid to determine an attribute of the specimen; or b) placing said collection device in a detection machine, manipulating said sealing assembly on said second output to release a specimen dissolved in said buffer fluid contained in said accommodating chamber of said collection device, and analyzing the specimen in the buffer fluid to determine an attribute of the specimen.

18. The collection device of claim 1, wherein said tubular wall of said filter member has an outer surface and said inlet member has an inner surface that defines said inlet passage, wherein said outer surface and said inner surface are in contact with each other to provide a sealing along the direction of said inlet passage between said filter member and said inlet member.

19. The collection device of claim 1, wherein said tubular wall of said filter member is made from rubber, such that said filter hole is expandable when a force is applied to said tubular wall.

20. The collection device of claim 1, wherein the diameter of said first output on said protrusion is about 0.8-1.5 mm, such that a predetermined amount of a liquid sample can be dispensed through said first output.

* * * * *